(12) United States Patent
Nabel et al.

(10) Patent No.: US 6,818,016 B1
(45) Date of Patent: Nov. 16, 2004

(54) METHODS FOR COATING STENTS WITH DNA AND EXPRESSION OF RECOMBINANT GENES FROM DNA COATED STENTS IN VIVO

(75) Inventors: Elizabeth G. Nabel, Ann Arbor, MI (US); Gary J. Nabel, Ann Arbor, MI (US); Zhi-yong Yang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 08/884,352

(22) Filed: Jun. 27, 1997

(51) Int. Cl.[7] .................................................. A61F 2/06
(52) U.S. Cl. ....................................... 623/1.42; 623/1.46
(58) Field of Search ............................. 604/19, 52, 53, 604/104; 606/195; 623/1, 11, 12, 900, 1.42, 1.43, 1.44, 1.45, 1.46, 1.47, 1.48

(56) References Cited

U.S. PATENT DOCUMENTS

| | | | |
|---|---|---|---|
| 5,292,321 A | | 3/1994 | Lee |
| 5,336,615 A | * | 8/1994 | Bell et al. ................. 435/240.2 |
| 5,383,928 A | * | 1/1995 | Scott et al. ................. 623/1.12 |
| 5,439,446 A | * | 8/1995 | Barry ............................ 604/53 |
| 5,443,827 A | * | 8/1995 | Haber et al. ............. 424/133.1 |
| 5,464,450 A | | 11/1995 | Buscemi et al. ................ 623/6 |
| 5,464,650 A | | 11/1995 | Berg et al. |
| 5,500,013 A | | 3/1996 | Buscemi et al. ................ 623/1 |
| 5,551,954 A | | 9/1996 | Buscemi et al. ................ 623/1 |
| 5,571,166 A | * | 11/1996 | Dinh et al. ...................... 623/1 |
| 5,588,962 A | * | 12/1996 | Nicholas et al. .............. 604/53 |
| 5,591,224 A | * | 1/1997 | Schwartz et al. ............... 623/1 |
| 5,591,227 A | | 1/1997 | Dinh et al. |
| 5,593,974 A | | 1/1997 | Rosenberg et al. |
| 5,628,785 A | * | 5/1997 | Schwartz et al. ........... 604/104 |
| 5,686,409 A | * | 11/1997 | McFadden et al. ......... 604/265 |
| 5,697,967 A | * | 12/1997 | Dinh et al. ................. 604/104 |
| 5,698,531 A | * | 12/1997 | Nabel et al. ................... 514/44 |
| 5,716,981 A | * | 2/1998 | Hunter et al. ............... 514/449 |
| 5,769,883 A | | 6/1998 | Buscemi et al. ................ 623/1 |
| 5,833,651 A | | 11/1998 | Donovan et al. ............. 604/53 |
| 6,071,305 A | * | 6/2000 | Brown et al. .............. 623/1.43 |
| 6,355,055 B1 | * | 3/2002 | Waksman et al. .......... 623/1.13 |

FOREIGN PATENT DOCUMENTS

| WO | WO 94/27612 | 12/1994 |
|---|---|---|
| WO | WO 95/25807 | 9/1995 |
| WO | WO 97/11720 | 4/1997 |

OTHER PUBLICATIONS

Yun–Wei Ye et al., Improved Bioresorbable Microporous Intravascular Stents for Gene Therapy; ASAIO Journal; 42:M823–M827, 1996.

* cited by examiner

*Primary Examiner*—Sharon Kennedy
(74) *Attorney, Agent, or Firm*—Brinks Hofer Gilson & Lione

(57) ABSTRACT

The present invention describes DNA coated stents and methods of using the same to treat or prevent vascular diseases, such as restenosis.

41 Claims, 1 Drawing Sheet

METHODS FOR COATING STENTS WITH DNA AND EXPRESSION OF RECOMBINANT GENES FROM DNA COATED STENTS IN VIVO

BACKGROUND OF THE INVENTION

1. Field of the Invention

This invention provides an intravascular DNA coated stent and methods for expressing recombinant genes in vivo using the DNA coated stent. DNA coated stents are useful for treating coronary and peripheral vascular diseases, particularly restenosis.

2. Background of the Invention

Coronary and peripheral angioplasty is routinely performed to treat obstructive atherosclerotic lesions in the coronary and peripheral blood vessels. Following balloon dilation of these blood vessels, 30–40% of patients undergo restenosis.

Restenosis is the reclosure of a peripheral or coronary artery following trauma to that artery caused by efforts to open a stenosed portion of the artery, such as, for example, by balloon dilation, ablation, atherectomy or laser treatment of the artery. Restenosis is believed to be a natural healing reaction to the injury of the arterial wall. The healing reaction begins with the thrombotic mechanism at the site of the injury. The final result of the complex steps of the healing process can be intimal hyperplasia, the uncontrolled migration and proliferation of medial smooth muscle cells, combined with their extracellular matrix production, until the artery is again stenosed or occluded. Thus, restenosis is characterized by both elastic recoil or chronic constriction of the vessel in addition to abnormal cell proliferation.

Currently restenosis must be treated with subsequent angioplasty procedures. In an attempt to prevent restenosis, metallic intravascular stents have been permanently implanted in coronary or peripheral vessels. For example, U.S. Pat. No. 5,304,122 (Schwartz et al.) describe metal stents useful for treating restenosis after balloon angioplasty or other coronary interventional procedures. The stent is typically inserted by catheter into a vascular lumen and expanded into contact with the diseased portion of the arterial wall, thereby providing mechanical support for the lumen. However, it has been found that restenosis can still occur with such stents in place; likely, because although the stent prevents elastic recoil of the artery, it fails to prevent the cell proliferation which leads to intimal hyperplasia. In addition, the stent itself can cause undesirable local thrombosis. To address the problem of thrombosis, persons receiving stents also receive extensive systemic treatment with anticoagulant and antiplatelet drugs.

Stents coated with various compositions have been proposed. For example, Dichek et al. (Circulation 1989, 80:1347–1353) describe coating stainless steel stents with sheep endothelial cells that had undergone retrovirus-mediated gene transfer for either bacterial β-galactosidase or human tissue-type plasminogen activator. The stents were studied ex vivo in tissue culture dishes only. The feasibility of implanting the stents into arteries were not explored. This procedure of coating stents with cells is tedious, cumbersome and costly because cell have to be derived from a patient.

Other methods of providing therapeutic substances to the vascular wall by means of stents have also been proposed. For example, WO 91/12779, entitled "Intraluminal Drug Eluting Prosthesis," and WO 90/13332, entitled "Stent With Sustained Drug Delivery," suggest coating stents with antiplatelet agents, anticoagulant agents, antimicrobial agents, anti-inflammatory agents, antimetabolic agents and other drugs to reduce the incidence of restenosis. Similarly, U.S. Pat. Nos. 5,571,166 and 5,554,182 (both to Dinh et al.) describe intraluminal stents coated with fibrin and heparin. The stent is used to treat restenosis.

SUMMARY OF THE INVENTION

Accordingly, one object of this invention is to provide an intravascular DNA coated stent.

A second object of this invention is to provide methods for expressing recombinant genes in vivo using the DNA coated stents.

A third object of this invention is to provide methods for treating coronary and peripheral vascular diseases, particularly restenosis and vein by-pass grafts, using the DNA coated stents.

The present inventors have now realized these and other objects through their discovery of methods for coating DNA on the outside surface of a stent.

DETAILED DESCRIPTION OF PREFERRED EMBODIMENTS

DNA Coated Stents

Figure 1:
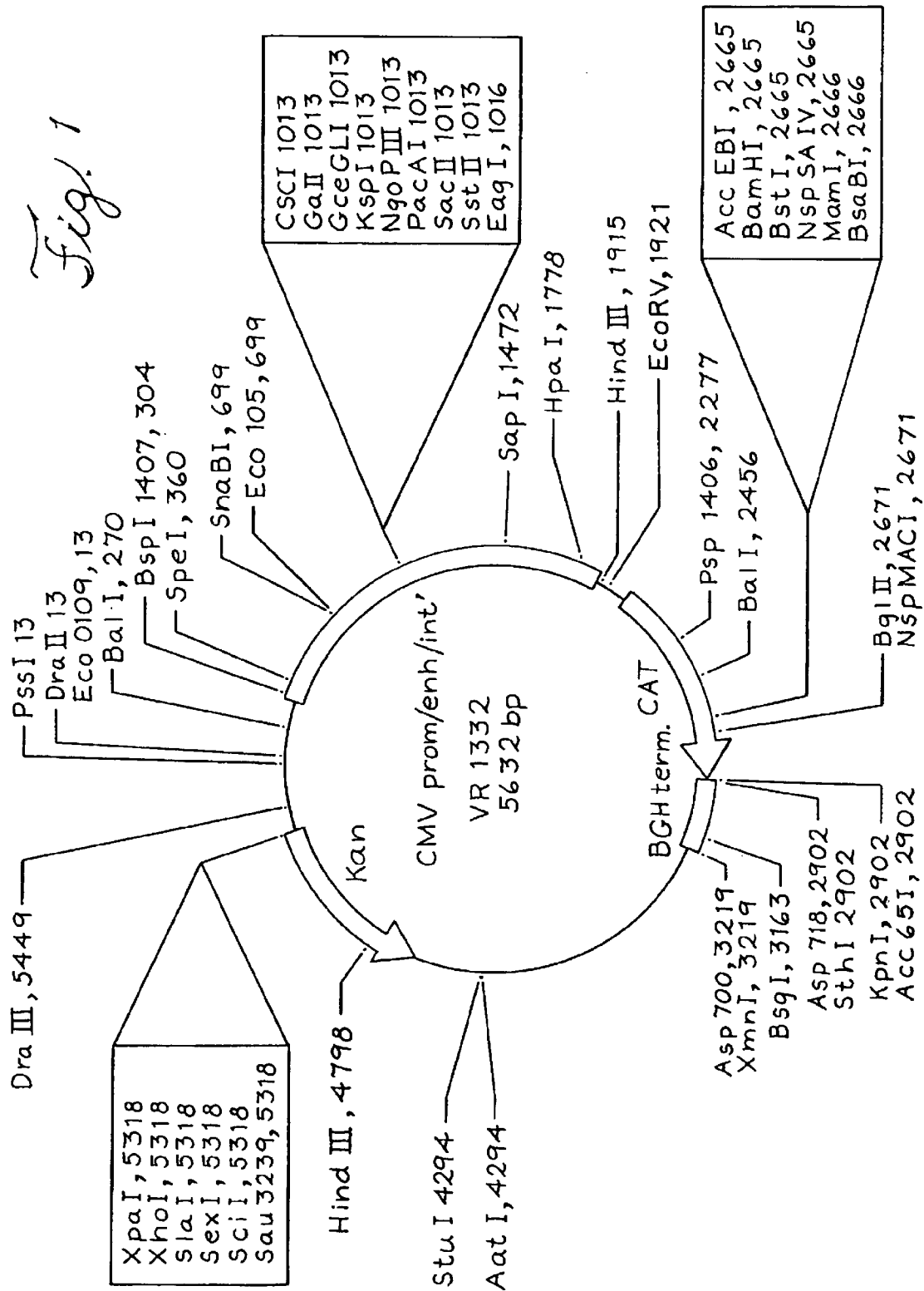
FIG. 1 is restriction map of plasmid pCMV-CAT (VR1332).

Stents are devices which can be delivered percutaneously to treat coronary artery occlusions and to seal dissections or aneurysms of splenic, carotid, iliac and popliteal vessels. Suitable stents useful in the invention are polymeric or metallic. Examples of polymeric stents include stents made with biostable or bioabsorbable polymers such as poly (ethylene terephthalate), polyacetal, poly(lactic acid), and poly(ethylene oxide)/poly(butylene terephthalate) copolymer. Examples of metallic stents include stents made from tantalum or stainless steel. Stents are available in myriad designs; all of which can be used in the present invention and are either commercially available or described in the literature. For example, a self-expanding stent of resilient polymeric material is described in WO 91/12779, entitled "Intraluminal Drug Eluting Prosthesis." Alternatively, U.S. Pat. No. 4,886,062 describes a deformable metal wire stent. Commercial sources of stents include Johnson & Johnson, Boston Scientific, Cordis, Advanced Catheter Systems, and U.S. Catheter, Inc.

Suitable genes which encode for therapeutic proteins useful in the invention include genes which encode anti-platelet agents, anticoagulant agents, antimitotic agents, antioxidants, antimetabolite agents, and anti-inflammatory agents. Preferred genes which encode therapeutic proteins include proteins which can inhibit proliferation of cells (particular of vascular smooth muscle cells (vsmc), including:

HSV thymidine kinase (McKnight, 1980, Nucleic Acids Res. 8:5949; Mansour et al., 1988, Nature 336:348–352), β-galactosidase, p16 (Chan et al., 1995, Mol. Cell. Biol. 15:2682–2688; Guan et al., Genes & Dev. 8:2939–2952), p21 (Harper et al., 1993, Cell 75:805; Xiong et al., 1993, Nature 366:701), p27 (Toyoshima et al., 1994, Cell 78:67–74; Polyak et al., 1994, Cell 78:59–66), p57 (Lee et al., 1995, Genes & Dev. 9:639–649; Matsuoka et al., 1995, Genes & Dev. 9:650–662), retinoblastoma (Rb) (see Chang et al., 1995, Science, 267:518) or its mutants (see for example, Hamel et al., 1992, Mol. Cell. Biol. 12:3431), and cytosine deaminase (WO 9428143; Wang et al., 1988, Can. Soc. Petrol. Geol. Mem., 14:71).

The sequences of these gene products are known in the literature. Any DNA encoding these gene products can be used, including the cDNA sequences that are described in the literature. Alternatively, fusion proteins of the above can be used. The preferred genes encode thymidine kinase (HSV-tk) or cytosine deaminase gene.

Any DNA encoding the above therapeutic proteins can be used. Preferably, the DNA sequence of the human cDNA encoding those proteins are used. The DNA can be naked or can be incorporated into a vector. Suitable vectors include shuttle vectors, expression vectors, retroviral vectors, adenoviral vectors, adeno-associated vectors and liposomes. Preferably a replication-defective adenovirus vector is used, such as pAd-BglII as described by Davidson et al. (1993, Nature Genet. 3:219–223). These vectors have been demonstrated to program high levels of expression of genes in balloon-injured rat carotid, rabbit coronary and porcine femoral arteries (Ohno et al., Science 255:781 (1994); Guzman et al:, Circulation 88:2838 (1993) and Barr et al., Gene Ther. 1:51 (1994)).

Various DNA constructs encoding HSV tk genes are available from American Type Culture Collection, Rockville, Md., including ATCC 39371, ATCC 39369 and VR-2036. Construction of adenoviral constructs containing HSV-tk is described in co-pending application Ser. No. 08/210,902, Example 1.

A list of preferred vectors is shown below in Table I.

TABLE 1

| Plasmid | Description |
| --- | --- |
| CMVtkcitep27 | CMVDSaClltk with cite-p27 (EcoRl-Xbal fragment from pcitep27) inserted at the Bglll site |
| CMVtkcitep27rev | CMVDSaClltk with CITE-p27rev (EcoRl-Xbal fragment from CITE p27rev) inserted into the BGlll site |
| CMVp27tk | pcMVp27citetk with the Aatll-Ncol fragment (containing cite) deleted. Tk and p27 are still active |
| CMVp27citetk | plasmid resulting from the ligation of 3 fragments: (1) Hindlll-EccRl from 1332DSacll (=CMVtk DSacll) + (2) Sall-Ncol from p27revcite + (3) Ncol-Hindlll from 1012-tk |
| CMVp27revcitetk | results from the ligation of 3 fragments: (1) Hindlll-EcoRl from 1332 DSacll + (2) Sall-Ncol from p27revcite + (3) Ncol-Hindlll from 1012-tk |
| CMVp27Sfcitetk | CMVp27citetk with the fragment Sacll-Fspl deleted. (region of p27 between the cdk2 binding site and the putative NLS) |
| CMvp27Nfcitetk | CMVP27 citetk with the fragment Narl-Fspl deleted. (region of p27 between the cdk2 binding site and the putative NLS) |
| CMVp27Afcitetk | CMVp27citetk with the fragment Avall-Fspl deleted. (region of p27 between the cdk2 binding site and the putative NLS) |
| CMVp27cdccitetk | CMVp27citetk with the cdc2 kinase consensus site mutated (TPKK to AAGG) |
| CMVp27SFtk | CMVp27tk with the Sacll-Fspl fragment deleted (that contains the region of p27 between the cdk2 binding site and the putative NLS) |

TABLE 1-continued

| Plasmid | Description |
| --- | --- |
| CMVp27NFtk | CMVp27tk with the Narl-Fspl fragment deleted (that contains the region of p27 between the cdk2 binding site and the putative NLS) |
| CMVp27Aftk | CMVp27tk with the Avall-Fspl fragment deleted (that contains the region of p27 between the cdk2 binding site and the putative NLS) |
| CMVp27SNtk | CMVp27citetk with the Sacll-Ncol fragment deleted (containing the C-terminus of p27) |
| CMVp27Sp21Ftk | CMVp27tk with the Hindlll-Ncol fragment from 1012-p21N inserted between the Sacll and Fspl sites |
| CMVp27Np21Ftk | CMVp27tk with the Hindlll-Ncol fragment from 1012-p21N inserted between the Narl and Fspl sites |
| CMVp27Sp21Fcitetk | CMVp27citetk with the Hindlll-Ncol fragment from 1012-p21N (containing the N-terminal part of p21 coding sequence) inserted between the Sacll and Fspl sites in the p27 coding region |
| CMVp27Np21Fcitetk | CMVp27citetk with the Hindlll-Ncol fragment from 1012-p21N inserted between the Narl and Fspl sites |
| CMVp27Sp21 | Clal-Sacll fragment from CMVp27citetk fused to the Ncol-Clal fragment of VR 1012-p21N (giving a fusion between p27N and p21N) |
| CMVp27Np21 | Clal-Narl fragment from CMVp27 citetk fused to the Ncol-Clal fragment of VR 1012-p21N (giving a fusion between p27N and p21N) |
| CMVp27Dkcitetk | CMVp27citetk with all K mutated to R between ATG and Sacll of p27. There is an additional 'c' before the Sacll site |
| CMVp27Ncitetk | CMVp27ctetk with a stop codon between Sacll and Xbal in p27 (only the N-terminus of p27 remains) |
| CMVp27NLScitetk | CMVp27citetk with a NLS (GRRRRA = ATF2 NLS) and a stop codon between Sacll and Xbal in p27 (only the N-terminus of p27 remains) |
| CMVp27DKNcitetk | CMVp27Dkcitetk with a stop codon between Sacll and Xbal in p27 (only the N-terminus of p27 remains) |
| CMVp27DKNLScitetk | CMVp27Dkcitetk with a NLS (GRRRRA = ATF2 NLS) and a stop codon between Sacll and Xbal in p27 (only the N-terminus of p27 remains) |

The stent can optionally be coated with other therapeutic proteins such as heparin, hirudin, angiopeptin, ACE inhibitors, growth factors (such as $IL_{2-10}$), nitric oxide or with DNA encoding the same.

Suitable polymerizable matrix useful for binding the DNA to the stent include any monomeric biocompatible material which can be suspended in water, mixed with DNA and subsequently polymerized to form a biocompatible solid coating. Thrombin polymerized fibrinogen (fibrin) is preferred.

The stent is preferably coated with about 50 µg to about 5 mg of DNA. The thickness of the polymerizable matrix containing the DNA is typically about 5–500 µm. The matrix preferably covers the entire surface of the stent.

Methods for Coating a Stent with DNA

Methods for coating surfaces are well known in the art and include, for example, spray coating, immersion coating, etc. Any of these methods can be used in the invention. For example, a liquid monomeric matrix can be mixed with the DNA and polymerization initiated. The stent can then be added to the polymerizing solution, such that polymer forms over its entire surface. The coated stent is then removed and dried. Multiple application steps can be used to provide improved coating uniformity and improved control over the amount of DNA applied to the stent.

In a preferred embodiment, an aqueous mixture of DNA and human thrombin is added to an aqueous suspension of fibrinogen. The fibrinogen concentration of the suspension is typically between about 10–50, preferably about 20–40, more preferably about 30 mg/ml. The concentration of the DNA in the aqueous mixture is typically about 1–20, preferably about 5–15, more preferably about 10 μg/ml. The amount of human thrombin in the aqueous mixture about 0.5 to 5, preferably about 1 U. The DNA and human thrombin are first added together to form a mixture and that mixture is then added to the fibrinogen suspension. Thereafter, a stent is dipped into the polymerizing solution. After the mixture solidifies, the stent is removed.

Methods for Placing the DNA Coated Stent within the Vasculature

The stent can be placed onto the balloon at a distal end of a balloon catheter and delivered by conventional percutaneous means (e.g. as in an angioplasty procedure) to the site of the restriction or closure to be treated where it can then be expanded into contact with the body lumen by inflating the balloon. The catheter can then be withdrawn, leaving the stent of the present invention in place at the treatment site. The stent may therefore provide both a supporting structure for the lumen at the site of treatment and also a site for instillation of DNA at the lumen wall. The site of instillation can be either an arterial or venous wall.

Site specific instillation of a solution of DNA at an arterial wall using a balloon catheter has previously been described by the present inventors in U.S. Pat. No. 5,698,531. Thus, the viability of incorporation of "naked DNA" into arterial cells and subsequent expression of that DNA has previously been demonstrated.

The stent can be placed in any peripheral or coronary artery or vein. The stent is preferably placed at the site of injury either immediately or soon after mechanical vessel injury.

Methods for Expressing Recombinant Genes in vivo Using the DNA Coated Stents

Recombinant genes can be expressed in vivo by implanting the DNA coated stents of the present invention in an artery or vein of a patient. Gene expression is continuous and can optionally be controlled with viral promoters or cell specific promoters such as smc, in particular sm 22α.

SM 22α is a putative calcium-binding protein that is expressed in cardiac, smooth and skeletal muscle lineages during mouse embryogenesis and in adult smcs (Lees-Miller et al., 1987, J. Biol. Chem. 262:2988; Duband et al., 1993, Differentiation, 55:1; Shanahan et al., 1993, Circ. Res. 73:193). Promoters of smcs are of particular interest because they direct transgene expression specifically in vascular and not visceral smooth muscle cells.

Method of Treating Coronary and Peripheral Vascular Diseases with the DNA Coated Stents Coronary and peripheral diseases, including restenosis, atherosclerosis, coronary artery bypass graft stenosis, vein bypass graft stenosis or restenosis, arterio-venous fistula stenosis or restenosis, peripheral artery stenosis or restenosis, can be treated by implanting the DNA coated stent of the present invention, into a coronary or peripheral artery or vein of a patient. Suitable patients include mammals such as dogs, horses, cattle, humans, etc. Humans are preferred patients.

In an alternate embodiment, the DNA coated stent is implanted into the patient and an antiplatelet agent, anticoagulant agent, antimicrobial agent, anti-inflammatory agent, antimetabolic agent, antimitotic agent or other drug is administered to reduce the incidence of restenosis. Suitable anticoagulant agents can include drugs such as heparin, coumadin, protamine, hirudin and tick anticoagulant protein. Suitable antimitotic agents and antimetabolite agents can include drugs such as colchicine, methotrexate, azathioprine, vincristine, vinblastine, fluorouracil, adriamycin and mutamycin. Ganciclovir or acyclovir is preferably administered.

Having generally described this invention, a further understanding can be obtained by reference to certain specific examples which are provided herein for purposes of illustration only and are not intended to be limiting unless otherwise specified.

EXAMPLES

Procedure for Coating the Stents Using Thrombin Polymerized Fibrinogen (Fibrin)

Human fibrinogen was dissolved in water at concentrations of 30 mg/ml. 100 μl of different concentrations of fibrinogen were used in the preparation. Fibrinogen was diluted in water when necessary and transferred to an Eppendorf tube.

Plasmid CAT (pCMV-CAT) was dissolved in water at concentrations of 10 mg/ml. The DNA was diluted in water in an Eppendorf tube to a final volume of 100 μg/ml. 1 U of human thrombin was added in the DNA solution and mixed gently.

The mixture of DNA and thrombin was added to the fibrinogen solution. After brief mixing, the mixture was loaded into Tygon tubing (⅛" ID; 1" to 1¼" long, Formulation S-50-HL) which was scaled at one end. A Johnson & Johnson metallic stent, 5.0 mm, was immediately inserted into the DNA/fibrinogen/thrombin mixture in the tubing, and incubated until the mixture solidified. The fibrin-coated stent was removed and air dried.

The coated stent was installed into the left and right pig iliac femoral arteries using routine surgical procedures.

Three days after installment of the stents, the arteries were excised, and homogenized using glass dowels. The protein extract was freeze-thawed 3×, heat-inactivated for 15 minutes at 65° C. and the supernatant was collected. 300 μg of the soluble protein was used for CAT assays. The results were read using a Betagen machine which measures the acetylation of CAT.

Implantation of the DNA Coated Stents in the Vasculature

Juvenile domestic pigs (3 months, 15–20 kg) of either sex are given aspirin (10 mg/kg) orally two days prior to surgery and three times weekly for the duration of the study.

Pigs were anesthetized using Telazol (6.0 mg/kg IM) and xylazine (2.2 mg/kg IM) and intubated with an endotracheal tube. 1% isofluane is administered throughout the surgical procedure. 150 units/kg of heparin were administered via IV prior to surgery.

Following prepping and draping, a midline abdominal incision was made, extending caudally to the pubis through the skin and fascia, and the abdominal musculature was divided in the midline. The peritoneal cavity was opened and the intestines retracted cranially using a Balfour retractor.

Using a combination of blunt and sharp dissection, each iliac and femoral artery was isolated from their cranial extent, caudally to beyond the bifurcation of the femoral artery.

The internal iliac artery was ligated at its most caudal point with 2-0 silk. Ties were looped around the proximal iliac and femoral arteries, then temporarily secured. An arteriotomy of the internal iliac artery was made just proximal to the ligature. The balloon-expandable stent was advanced to the iliac artery and the balloon inflated using an inflation device at pressure of 6 atmospheres. The balloon was deflated and the balloon catheter removed, then the internal iliac artery was ligated followed by release of the loops. Restoration of arterial blood flow was confirmed. The peritoneum and the muscle were closed with 1-0 vicryl continuous sutures, and the fascial layer closed with 1-0 vicryl interrupted sutures. The skin was closed with staples.

Results

The following data demonstrate the expression of the reporter gene, CAT, in porcine arteries in vivo following implantation of the DNA coated stent.

|   | Fibrinogen (mg) | Reporter DNA (µg) | % CAT activity | days after stent placement |
|---|---|---|---|---|
| 1 | 15 | 100 | 8.4, 23.1, 6.2 | 3 |
|   | 15 | 500 | 7.5, 3.9 | 3 |
|   | 15 | 1000 | 2.0 | 3 |
| 2 | 15 | 100 | 3.4 | 7 |
| 3 | 15 | 100 | 2.54 | 10 |
| 4 | 10 | 100 | 2.8 | 3 |
| 5 | 10 | 100 | 0.9 | 10 |

The above data was used to determine the optimal dose of DNA and fibrinogen. This data supports the principle that DNA coated stents can be implanted in a patient, the gene is expressed as a protein, and sufficient quantities of protein are produced to allow measurement thereof.

Having now fully described the invention, it will be apparent to one of ordinary skill in the art that many changes and modifications can be made thereto without departing from the spirit or scope of the invention as set forth herein.

What is claimed is:

1. An implantable device comprising a biostable intravascular stent coated with a polymer matrix and DNA encoding a therapeutically useful protein, said DNA being uniformly dispersed within said matrix.

2. The implantable device of claim 1, wherein the stent is a polymeric or metallic stent.

3. The implantable device of claim 2, wherein the stent is stainless steel.

4. The implantable device of claim 1, wherein the therapeutically useful protein is an antiplatelet agent, anticoagulant agent, antimitotic agent, antioxidant, antimetabolite agent, or anti-inflammatory agent.

5. The implantable device of claim 1, wherein the therapeutically useful protein inhibits the proliferation of cells.

6. The implantable device of claim 1, wherein the therapeutically useful protein is thymidine kinase, p16, p21, p27, p57, retinoblastoma or cytosine deaminase.

7. The implantable device of claim 6, wherein the therapeutically useful protein is thymidine kinase or cytosine deaminase.

8. The implantable device of claim 1, wherein the stent is coated with about 50 µg to about 5 mg of DNA.

9. The implantable device of claim 1, wherein the polymer matrix comprises fibrin.

10. The implantable device of claim 2, wherein the stent is a polymeric stent comprising a polymer selected from the group consisting of poly(ethylene terephthalate), polyacetal, and poly(ethylene oxide)/poly(butylene terephthalate) copolymer.

11. The implantable device of claim 1, wherein the DNA is naked DNA.

12. The implantable device of claim 1, wherein the DNA is incorporated into a vector.

13. The implantable device of claim 12, wherein the vector is selected from the group consisting of shuttle vectors, expression vectors, retroviral vectors, adenoviral vectors, adeno-associated vectors and liposomes.

14. The implantable device of claim 1, wherein the polymer matrix is formed from an aqueous suspension of DNA and liquid monomeric matrix.

15. The implantable device of claim 1, wherein the DNA comprises an sm 22α promoter operatively linked to the DNA encoding the therapeutically useful protein.

16. The implantable device of claim 1, wherein the therapeutically useful protein is a fusion protein.

17. An implantable device comprising an intravascular stent comprising a biostable material and coated with a polymer matrix and DNA encoding a therapeutically useful protein.

18. The implantable device of claim 17, wherein the stent is a polymeric or metallic stent.

19. The implantable device of claim 18, wherein the stent is stainless steel.

20. The implantable device of claim 17, wherein the therapeutically useful protein is an antiplatelet agent, anticoagulant agent, antimitotic agent, antioxidant, antimetabolite agent, or anti-inflammatory agent.

21. The implantable device of claim 17, wherein the therapeutically useful protein inhibits the proliferation of cells.

22. The implantable device of claim 17, wherein the therapeutically useful protein is thymidine kinase, p16, p21, p27, p57, retinoblastoma or cytosine deaminase.

23. The implantable device of claim 22, wherein the therapeutically useful protein is thymidine kinase or cytosine deaminase.

24. The implantable device of claim 17, wherein the stent is coated with about 50 µg to about 5 mg of DNA.

25. The implantable device of claim 17, wherein the polymer matrix comprises fibrin.

26. The implantable device of claim 18, wherein the stent is a polymeric stent comprising a polymer selected from the group consisting of poly(ethylene terephthalate), polyacetal, and poly(ethylene oxide)/poly(butylene terephthalate) copolymer.

27. The implantable device of claim 17, wherein the DNA is naked DNA.

28. The implantable device of claim 17, wherein the DNA is incorporated into a vector.

29. The implantable device of claim 28, wherein the vector is selected from the group consisting of shuttle vectors, expression vectors, retroviral vectors, adenoviral vectors, adeno-associated vectors and liposomes.

30. The implantable device of claim 17, wherein the polymer matrix is formed from an aqueous suspension of DNA and liquid monomeric matrix.

31. The implantable device of claim 17, wherein the DNA comprises an sm 22α promoter operatively linked to the DNA encoding the therapeutically useful protein.

32. The implantable device of claim 17, wherein the therapeutically useful protein is a fusion protein.

33. An implantable device comprising a biostable intravascular stent coated with a polymer matrix and DNA encoding a therapeutically useful protein, said DNA being in contact with said polymer matrix.

34. The implantable device of claim 33, wherein the stent is a polymeric or metallic stent.

35. The implantable device of claim 34, wherein the stent is stainless steel.

36. The implantable device of claim 33, wherein the therapeutically useful protein is an antiplatelet agent, anticoagulant agent, antimitotic agent, antioxidant, antimetabolite agent, or anti-inflammatory agent.

37. The implantable device of claim 33, wherein the therapeutically useful protein inhibits the proliferation of cells.

38. The implantable device of claim 33, wherein the therapeutically useful protein is thymidine kinase, p16, p21, p27, p57 retinoblastoma, protein or cytosine deaminase.

39. The implantable device of claim 38, wherein the therapeutically useful protein is thymidine kinase or cytosine deaminase.

40. The implantable device of claim 33, wherein the stent is in contact with about 50 µg to about 5 mg of DNA.

41. The implantable device of claim 33, wherein the polymer matrix comprises fibrin.

* * * * *